United States Patent
Bias

(10) Patent No.: US 7,923,044 B2
(45) Date of Patent: Apr. 12, 2011

(54) COMPOSITION FOR HIGH-ORAC VALUE DIETARY SUPPLEMENT

(75) Inventor: Scott Bias, Huntington Beach, CA (US)

(73) Assignee: Paradise Herbs & Essentials, Inc., Huntington Beach, CA (US)

( * ) Notice: Subject to any disclaimer, the term of this patent is extended or adjusted under 35 U.S.C. 154(b) by 0 days.

(21) Appl. No.: 12/503,575

(22) Filed: Jul. 15, 2009

(65) Prior Publication Data

US 2010/0015109 A1    Jan. 21, 2010

Related U.S. Application Data

(60) Provisional application No. 61/080,857, filed on Jul. 15, 2008.

(51) Int. Cl.
```
A61K 36/00      (2006.01)
A61K 36/54      (2006.01)
A61K 36/8998    (2006.01)
A61K 36/31      (2006.01)
A61K 36/81      (2006.01)
A61K 36/815     (2006.01)
A61K 36/068     (2006.01)
A61K 31/733     (2006.01)
A61K 36/45      (2006.01)
A61K 36/424     (2006.01)
A61K 36/481     (2006.01)
A61K 36/236     (2006.01)
A61K 36/268     (2006.01)
A61K 36/79      (2006.01)
A61K 36/9066    (2006.01)
A61K 36/06      (2006.01)
A61K 36/02      (2006.01)
A61K 31/34      (2006.01)
A61K 31/03      (2006.01)
A61K 31/045     (2006.01)
A61K 31/015     (2006.01)
A61K 31/05      (2006.01)
A61K 31/025     (2006.01)
```
(52) U.S. Cl. ........ 424/725; 424/93.45; 424/195.15; 424/195.17; 424/750; 424/739; 424/765; 424/732; 424/729; 424/766; 424/757; 424/756; 514/474

(58) Field of Classification Search ............ None
See application file for complete search history.

(56) References Cited

U.S. PATENT DOCUMENTS

| | | | |
|---|---|---|---|
| 5,744,187 A * | 4/1998 | Gaynor | 426/599 |
| 6,210,701 B1 | 4/2001 | Darland et al. | |
| 6,231,866 B1 | 5/2001 | Mann | |
| 6,323,238 B1 | 11/2001 | Yoo et al. | |
| 6,440,410 B1 | 8/2002 | Yegorova | |
| 6,440,467 B2 | 8/2002 | Mann | |
| 6,569,683 B1 | 5/2003 | Ochi et al. | |
| 6,602,517 B2 | 8/2003 | Darland et al. | |
| 6,753,312 B2 | 6/2004 | Yatcilla et al. | |
| 6,841,060 B2 | 1/2005 | Shanbrom | |
| 6,884,783 B2 | 4/2005 | Jia et al. | |
| 6,989,161 B2 | 1/2006 | Roufs et al. | |
| 7,132,296 B2 | 11/2006 | Ou et al. | |
| 7,175,862 B2 | 2/2007 | Pusateri et al. | |
| 7,226,626 B2 | 6/2007 | Yatcilla et al. | |
| 7,294,351 B2 | 11/2007 | Hudnall | |
| 7,371,389 B2 | 5/2008 | Keefe et al. | |
| 2004/0161422 A1 * | 8/2004 | Ranganathan | 424/93.45 |
| 2005/0013902 A1 | 1/2005 | Pearce | |
| 2006/0210609 A1 * | 9/2006 | Mower | 424/439 |

OTHER PUBLICATIONS

Dhuley, Anti-oxidant effects of cinnamon (Cinnamomum verum) bark and greater cardamom (Amomum subulatum) seeds in rats fed high fat diet, Indian Journal of Experimental Biology, 37: 238-242.*
Mabeau et al, Antioxidant activity of artichoke extracts and by-products, Acta Horticulturae (2006), Volume Date 2007, 730(Proceedings of the VI International Symposium on Artichoke, Cardoon and Their Wild Relatives, 2006), 491-496.*

* cited by examiner

*Primary Examiner* — Qiuwen Mi
(74) *Attorney, Agent, or Firm* — Amin Talati, LLC

(57) ABSTRACT

A dietary supplement composition having an ORAC value in excess of at least about 2,500 and which can be readily consumed in a small quantity is provided for supplementing an individual's daily intake. The dietary supplement composition suitably includes organic and/or vegan ingredients and can be consumed in quantities of as little as about 1 tablespoon to provide an amount of antioxidants equivalent to at least the minimum recommended daily intake of five to nine servings of fruits and/or vegetables.

19 Claims, No Drawings

COMPOSITION FOR HIGH-ORAC VALUE DIETARY SUPPLEMENT

This application claims the benefit of earlier filed U.S. Patent Application Ser. No. 61/080,857 filed on Jul. 15, 2008.

FIELD OF THE INVENTION

The present invention relates to a composition with a high Oxygen Radical Absorbance Capacity (ORAC) value for reducing cellular damage and premature aging caused by free-radicals.

BACKGROUND OF THE INVENTION

The development of many chronic and degenerative diseases, such as cancer, heart disease, and neuronal degeneration, such as Alzheimer's and Parkinson's disease has been theorized to be caused, in part, by oxidative stress. Oxidative stress has also been implicated in the process of aging. It is known that reactive oxygen species can damage biological molecules such as proteins, lipids, and DNA. While the human body has developed a number of systems to eliminate free radicals from a person's system, it is not 100% efficient.

Diets rich in fruits and vegetables have long been considered to be an excellent source of antioxidants. Oxygen Radical Absorbance Capacity (ORAC) measures the antioxidant power and activity of a given product or food; the higher the ORAC value, the greater the antioxidant protection against free radicals that can cause cellular damage and premature aging. Studies show high ORAC foods may be essential in helping the body maintain optimal health and well-being. However, many individuals do not consume sufficient quantities of the recommended five to nine servings of fruits and vegetables per day for various reasons. Thus, there is a need and a desire for a dietary supplement having a high ORAC value or an ORAC value in excess of at least about 2,500 (i.e., about five servings of fruits and vegetables) that can be readily consumed in a small quantity to increase an individual's level of health.

SUMMARY OF THE INVENTION

A general object of the present invention is to provide a high Oxygen Radical Absorbance Capacity (ORAC) value composition which is all natural.

A more specific object of the present invention is to provide a dietary supplement composition having an ORAC value in excess of at least about 2,500 which can be readily consumed in a small quantity.

Another object of the present invention is to provide a dietary supplement composition having an ORAC value equivalent to at least the minimum recommended daily intake of five to nine servings of fruits and/or vegetables and which can be readily mixed with or dissolved in other foods.

A further object of the present invention it to provide a 100% vegan composition that contains no animal products, common allergens, added sweeteners, or flavored fillers.

A still further object of the present invention is to provide a composition containing a variety of organic and pesticide-free ingredients.

The prior art generally fails to provide a composition, useful as a dietary supplement, containing an antioxidant equivalent of at least the recommended daily number servings of fruits and vegetables provided in an easy to ingest serving. Accordingly, a dietary supplement composition, which can be readily consumed in a small quantity, has been developed to provide an antioxidant equivalent of at least five servings and, advantageously, greater than about nine servings of fruits and vegetables.

In one embodiment of the present invention, a dietary supplement composition having an ORAC value in excess of about 4,500 can include and/or consist of green grass juice powder, green and/or blue-green algae, vegetables, a source of vitamin C, oat bran, a source of beta-glucans, probiotic organisms, fruits such as, for example, berries, a source of polyphenols, a source of oligomeric proanthocyanidins, a source of silymarin, a source of chlorogenic acids, an adaptogenic herb, superfoods, medicinal rhizomes, cinnamon bark, and combinations thereof.

In another embodiment of the present invention a high-ORAC value composition includes and/or consists of wheat grass, Egyptian wheat grass, alfalfa grass, barley grass, oat grass, spirulina, chlorella, spinach, broccoli, parsely, kale, tomato, acerola berry, camu camu berry, amla berry, quercetin, acai berry, lycium berry, agaricus, cordyceps, maitake, reishi, shiitake, *Lactobacillus acidophilus*, *Lactobacillus casei rhamnosus*, *Bifidobacterium longum*, *Streptococcus thermophilus*, and *Lactobacillus plantarum*, oat beta-glucan fiber, beet fiber, inulin fructooligosaccharides (FOS), strawberry, raspberry, blueberry, cherry, pomegranate, cranberry, green tea, white tea, grape seed, artichoke, milk thistle, eleuthero root bark, rhodiola root, gynostemma aerial part, holy basil leaf, ashwagandha root, astragalus root, schisandra berry, ginseng root, suma root, licorice root, ginger, maca root, tumeric rhizome, and cinnamon.

As used herein, the term "high-ORAC value" refers to a composition, formulation, or dietary supplement which has an oxygen radical absorbance capacity, as measured by known methods, of at least about 4,500 or the equivalent of at least about nine servings of fruits and/or vegetables. Generally, one serving of fruits and/or vegetables has an average ORAC value of about 500. An example of a high-ORAC value composition in accordance with the invention is a formulation which provides the antioxidant equivalent of twenty-four servings of fruits and/or vegetables, i.e., has an ORAC value of about 12,000.

As used herein, the term "about" when used in connection with a numerical value refers to a range of values falling within ±10% of the numerical value. For example, an ORAC value of about 9,000 includes ORAC values falling in the range of 8,100 to 9,900.

As used herein the terms "adaptogens" and "adaptogenic herbs" refer to natural herb products that include or contain antioxidants in addition to one or more triterpenes (e.g., triterpenoid saponins, phytosterols and phytoecdysteroids), phenyl propanes (e.g., flavanoids and lignans), and/or oxylipins (e.g., hydroxylated fatty acids). Adaptogenic herbs and/or adaptogens are believed to increase the body's resistance to stress, trauma, anxiety, and fatigue. Examples of adaptogens include Asian ginseng (*Panax ginseng*), American ginseng (*Panax quinquefolius*), Siberian ginseng (*Eleutherococcus senticosus*), Suma (*Pfaffia paniculata*), Ashwagandha (*Withania somnifera*), Astragalus (*Astragalus* spp.), Licorice root (*Glycyrrhiza glabra* and *G. uralensis*), Schisandra (*Schisandra chinensis*), Jiaogulan (*Gynostemma pentaphyllum*), amla (*Emblica officinalis*), eleuthero (*Eleutherococcus senticosus*), golden root (*Rhodiola rosea*), jiaogulan (*Gynostemma pentaphyllum*), reishi (*Ganoderma lucidum*), holy basil (*Ocimum sanctum*), goji (*Lycium Barbarum*), cordyceps (*Cordyceps sinensis*), licorice (*Glycyrrhiza glabra*), and ginger (*Zingiber officinale*).

As used herein the term "superfood" refers to foods having a high phytonutrient content (i.e., containing high concentrations of one or more plant-derived compounds). Examples of superfoods include, but are not limited to, acai berries, maca root, wheat grass, barley grass, alfalfa grass, oat grass, Egyptian wheat grass, spirulina, chlorella, blackcurrants, cacao, honey, bee pollen, bilberry, coffee berry, aloe vera, noni fruit, yacon root, rose hips, watercress, papaya, soy, flax seed, alfalfa sprouts, broccoli, oranges, spinach, tomatoes, walnuts, avocado, and quinoa.

This and other embodiments of the present invention are more fully described in connection with the detailed description.

DETAILED DESCRIPTION OF THE INVENTION

Generally, the human body supplements antioxidants found in the body with antioxidants from a well-balanced diet. Antioxidants are necessary to eliminate free radicals from the body, which are known to damage biological molecules such as proteins, lipids, and DNA. In addition, oxidative stress has been theorized to cause, in part, degenerative diseases such as cancer and heart disease, and neuronal degeneration such as Alzheimer's and Parkinson's disease. Many individuals do not eat a well-balanced diet; they have a need for antioxidant supplementation. Accordingly, a high-ORAC value composition has been developed which is designed to be a safe and natural dietary supplement to provide the antioxidant equivalent of at least about nine servings of fruit and vegetables (i.e., an ORAC value of at least about 4,500).

In one embodiment of the present invention, a single tablespoon (six grams) of the high-ORAC composition has a value of over 12,000 ORAC, the equivalent of 24 servings of fruits and vegetables in antioxidant capacity.

In another embodiment of the present invention, the high-ORAC composition comprises over 42 certified organic and pesticide-free ingredients, including highly bioavailable juice powders, freeze-dried berries and vegetables, and ecologically wild crafted or naturally grown herbal concentrates.

In one embodiment of the present invention, a dietary supplement composition having an ORAC value in excess of about 4,500 can include and/or consist of green grass juice powder, green and/or blue-green algae, vegetables, a source of vitamin C, oat bran, a source of beta-glucans, a probiotic, fruits such as, for example, berries, a source of polyphenols, a source of oligomeric proanthocyanidins (OPCs), a source of silymarin, a source of chlorogenic acids, an adaptogenic herb, a superfood, a medicinal rhizome, cinnamon bark, and combinations thereof.

Powdered grass juices, which provide bioavailable nutrients, can be derived, for example, from one or more species of green grasses including, but not limited to, wheat grass, Egyptian wheat grass, alfalfa grass, barley grass, and oat grass.

Green and/or blue-green algae can also be included in the high-ORAC composition. One suitable green algae species that can be included is chlorella. An example of a suitable blue-green algae includes spirulina.

The composition can also include antioxidants and nutrients, which can be derived from vegetables such as, for example, broccoli sprout, spinach, parsley, kale, tomatoes, and combinations thereof. Suitably, the vegetables have been freeze-dried.

Suitable sources of vitamin C for use in the present invention include, but are not limited to, acerola berry, camu camu berry, amla berry, acai berry, lycium berry (Goji berry), and combinations thereof.

Beta-glucans can be provided by hot water extracts of one or more mushroom fruiting bodies. Suitable sources of beta-glucans can include, for example, mushroom species selected from agaricus (i.e., edible species of the *Agaricus* genus), cordyceps (*Cordyceps sinensis*), maitake (*Grifola frondosa*), reishi (*Ganoderma lucidum*), shiitake (*Lentinula edodes*), and combinations thereof.

Advantageously, the composition can include one or more probiotics such as, for example, lactic acid bacteria or prebiotic ingredients. In one embodiment, the composition can include lactic acid bacteria, such as, for example, *Lactobacillus acidophilus, Lactobacillus casei rhamnosus, Bifidobacterium longum, Streptococcus thermophilus, Lactobacillus plantarum*, and combinations thereof. Examples of prebiotic ingredients which can be used alone or in combination with lactic acid bacteria include, but are not limited to, oat beta-glucan fiber, beet fiber, inulin FOS (chicory), and combinations thereof.

Antioxidants and nutrients can also be provided by including one or more fruits in the composition. Suitably, the fruits have been freeze-dried. Examples of suitable fruits, particularly berries, include, but are not limited to, strawberries, raspberries, blueberries, cherries, pomegranates, cranberries, and blends thereof.

Sources of polyphenols and oligomeric proanthocyanidins (OPC's) which can be used in the composition include, but are not limited to, green and/or white teas and grape seed extract, respectively.

Flavonoids are plant polyphenols found as the pigments in leaves, barks, rinds, seeds, and flowers. Flavonoids are important for human health and, like vitamins, these compounds are not produced endogenously by the body. Quercetin has shown the greatest activity among the flavonoids studied in experimental models and is frequently used therapeutically in allergic conditions, including asthma, hayfever, eczema, and hives. Additional clinical uses include treatment of gout, pancreatitis, and prostatitis, which are also, in part, inflammatory conditions. The common link is its ability to mediate production and manufacture of pro-inflammatory compounds. However, its uses also may be important in cancer therapeutics. Quercetin is a recognized antioxidant and has been studied for its gastro-protective effects, inhibition of carcinogenicity either alone or in combination with chemotherapeutic agents, reducing risk of cataract. Sources of quercetin include, but are not limited to, green vegetables, berries, onions, parsley, legumes, green tea, citrus fruits, and red grape wines.

Sources of silymarin and chlorogenic acids, which are believed to provide support for hepatic function and health, include, for example, milk thistle seed extract and artichoke leaf extract, respectively.

As noted above, compositions in accordance with present invention can also include one or more adaptogenic herbs and/or superfoods. Examples of suitable adaptogenic herbs include, but are not limited to, Eleuthero root bark, Rhodiola root, Jiaogulan/Gynostemma aerial part, Reishi fruiting body, Holy Basil leaf, Ashwagandha root, Astragalus root, Schisandra berry, Cordyceps Cs-4, American Ginseng, Suma root, Licorice root, Ginger rhizome, and Tangerine peel. Examples of suitable superfoods include, but are not limited to, acai berry and/or maca root.

Medicinal rhizomes such as, for example, ginger rhizome and/or tumeric rhizome can also be included in a composition in accordance with the present invention.

In another embodiment of the invention, a high-ORAC composition can include or consist of:
 about 20% to about 30% powdered grass juices;
 about 20% to about 25% algae;

about 10% to about 15% freeze-dried vegetable matter;
about 10% to about 15% of a blend of a source of vitamin C and a source of quercetin;
about 5% to about 10% oat bran;
about 2% to about 6% of a source of beta-glucans;
about 2% to about 6% of a probiotic and prebiotic;
about 1% to about 5% freeze-dried fruit;
about 1% to about 5% of a blend of a source of polyphenols and a source of OPC's;
about 1% to about 5% of a blend of a source of silymarin and a source of chlorogenic acids;
about 1% to about 5% of an adaptogenic herb;
about 1% to about 5% of a superfood; and
about 1% to about 5% of a blend of a medicinal rhizome and cinnamon bark.

In accordance with a further embodiment of the invention, a composition having an ORAC value of about 12,000 can include and/or consist of, in about a 6 gram dosage:
at least about 1560 milligrams (mg) of powdered grass juices;
at least about 1125 mg algae;
at least about 830 mg freeze-dried vegetable matter;
at least about 812 mg of a blend of a source of vitamin C and a source of quercetin;
at least about 500 mg oat bran;
at least about 250 mg of a source of beta-glucans;
at least about 250 mg of probiotics;
at least about 125 mg freeze-dried fruit;
at least about 125 mg of a blend of a source of polyphenols and a source of OPC's;
at least about 125 mg of a blend of a source of silymarin and a source of chlorogenic acids;
at least about 125 mg of an adaptogenic herb;
at least about 125 mg of a superfood; and
at least about 125 mg of a blend of a medicinal rhizome and cinnamon bark.

The powdered grass juices can include a blend of:
at least about 312 mg organic Wheat grass (young leaf);
at least about 312 mg organic Egyptian Wheat grass (*Triticum polonicum*);
at least about 312 mg organic Alfalfa grass (young leaf);
at least about 312 mg organic Barley grass (young leaf); and
at least about 312 mg organic Oat grass (young leaf).

The algae can include a blend of:
at least about 625 mg organic Spirulina; and
at least about 500 mg Chlorella (pharmaceutical-grade, pesticide-free, soft-cell).

The freeze-dried vegetable matter can include a blend of:
at least about 125 mg organic Spinach (freeze-dried);
at least about 125 mg organic broccoli sprout (freeze-dried);
at least about 170 mg organic parsley (freeze-dried);
at least about 125 mg Kale (freeze-dried); and
at least about 285 mg organic tomato.

The source of vitamin C can include a blend of Acerola berry, Camu Camu berry, Amla berry, Acai berry, and/or Goji/Lycium berry.

The source of beta-glucans can include a blend of:
at least about 50 mg Agaricus fruiting body;
at least about 50 mg *Cordyceps* CS-4;
at least about 50 mg Maitake fruiting body;
at least about 50 mg Reishi fruiting body; and
at least about 50 mg Shiitake fruiting body;

The probiotics can include a blend or lactic acid bacteria species including *L. Acidophilus, L. Casei Rhamnosus, B. Longum, S. Thermophilus*, and/or *L. Planatarum*, in combination with oat beta-glucan fiber, beet fiber, and inulin FOS (Chicory).

The freeze-dried fruits can include a blend of organic strawberry, raspberry, blueberry, tart cherry, pomegranate, and cranberry.

The source of polyphenols can include at least about 62.5 mg of organic green and/or white tea. The source of OPC's can include at least about 62.5 mg of grape seed extract.

The source of silymarin can includes at least about 62.5 mg of milk thistle seed extract while the source of chlorogenic acids can include at least about 62.5 mg of artichoke leaf extract.

The adaptogenic herb can be a blend of herbs including Eleuthero root bark, Rhodiola root, Jiaogulan/Gynostemma aerial part, Reishi fruiting body, Holy Basil leaf, Ashwagandha root, Astragalus root, Schisandra berry, Cordyceps Cs-4, American Ginseng, Suma root, Licorice root, Ginger rhizome, and Tangerine peel.

The superfood can include at least about 62.5 mg of Acai berry and at least about 62.5 mg of Maca root.

The medicinal rhizome can include a combination of Ginger rhizome and Tumeric rhizome.

A method for administering a high-ORAC dietary supplement composition to a human includes oral ingestion of the dietary supplement composition in any appropriate form such as, for example, a powder, a liquid, or a suspension or dispersion of a powdered form of the composition into a suitable carrier liquid such as, for example, water and/or a fruit or vegetable juice.

Powdered forms of the dietary supplement composition can be pressed into a tablet. The powder can also be encapsulated, using any edible material, to form a capsule, caplet, soft gel capsule or other encapsulated product, for oral administration.

Liquid forms of the dietary supplement composition can be provided as concentrates which can be further diluted with an ingestible liquid such as, for example, water, fruit juice and/or vegetable juice. Liquid forms of the dietary supplement composition can further be provided as gels or pastes which can be ingested directly, dissolved, dispersed, or suspended in an ingestible carrier liquid, or encapsulated in a suitable capsule.

In accordance with one embodiment, a high-ORAC dietary supplement composition powder can be prepared for ingestion by dissolving it in a liquid. The serving amount can vary based upon the amount of dietary supplement composition that is necessary to achieve the desired antioxidant equivalent to a certain number of servings of fruits and vegetables. For example, using a high-ORAC composition having an average ORAC value of about 2,000 per gram, about 250 mg (about ⅛ of a teaspoon) of the formulation can be ingested to provide one serving of fruits and vegetables.

In certain embodiments, about six grams or about one tablespoon of a high-ORAC composition can be dissolved or dispersed in about 237 milliliters (about 8 fluid ounces) of an ingestible carrier liquid such as, for example, water, fruit juice, and/or vegetable juice.

In accordance with one embodiment a method for supplementing an individual's diet to provide a daily recommended amount of antioxidants includes administering to the individual an effective amount of a high ORAC composition wherein the composition has an ORAC value of at least about 4,500. Suitably, a serving of the composition provides an equivalent of about twenty-four servings of fruits and/or vegetables or an ORAC value of at least about 12,000.

While in the foregoing specification this invention has been described in relation to certain preferred embodiments thereof, and many details have been set forth for the purpose of illustration, it will be apparent to those skilled in the art that the invention is susceptible to additional embodiments and that certain details described herein can be varied considerably without departing from the basic principles of the invention.

What is claimed is:

1. A composition having a high Oxygen Radical Absorbance Capacity (ORAC) value, comprising:
    about 20% to about 30% powdered grass juices;
    about 20% to about 25% algae;
    about 10% to about 15% freeze-dried vegetable matter;
    about 10% to about 15% of a blend of a source of vitamin C and a source of quercetin;
    about 5% to about 10% oat bran;
    about 2% to about 6% of a source of beta-glucans;
    about 2% to about 6% of a probiotic and a prebiotic;
    about 1% to about 5% freeze-dried fruit;
    about 1% to about 5% of a blend of a source of polyphenols and a source of oligomeric proanthocyanidins (OPCs);
    about 1% to about 5% of a blend of a source of silymarin and a source of chlorogenic acids;
    about 1% to about 5% of an adaptogenic herb;
    about 1% to about 5% of a superfood; and
    about 1% to about 5% of a blend of a medicinal rhizome and cinnamon bark;
    wherein the ORAC value of a serving of the composition exceeds 4,500.

2. A composition with a high Oxygen Radical Absorbance Capacity (ORAC) value, consisting of:
    about 312 mg wheat grass;
    about 312 mg Egyptian wheat grass (*Triticum polonicum*);
    about 312 mg alfalfa grass;
    about 312 mg barley grass;
    about 312 mg oat grass;
    about 625 mg spirulina;
    about 500 mg chlorella;
    about 125 mg spinach;
    about 125 mg broccoli sprout;
    about 170 mg organic parsley;
    about 125 mg kale;
    about 285 mg tomato;
    about 812 mg of a blend of acerola berry, camu camu berry, amla berry, acai berry, lycium berry, and quercitin;
    about 500 mg oat bran;
    about 50 mg agaricus fruiting body;
    about 50 mg cordyceps;
    about 50 mg maitake fruiting body;
    about 50 mg reishi fruiting body;
    about 50 mg shiitake fruiting body;
    about 250 mg of a blend of *Lactobacillus acidophilus, Lactobacillus casei rhamnosus, Bifidobacterium longum, Streptococcus thermophilus, Lactobacillus plantarum*, oat beta-glucan, beet fiber, and inulin;
    about 125 mg of a blend of strawberry, raspberry, blueberry, tart cherry, pomegranate, and cranberry;
    about 62.5 mg of green and white tea extract;
    about 62.5 mg of grape seed extract;
    about 62.5 mg of milk thistle extract;
    about 62.5 mg of artichoke leaf extract;
    about 125 mg of a blend of eleuthero root bark, rhodiola root, jiaogulan/gynostemma aerial part, reishi fruiting body, holy basil leaf, ashwagandha root, astragalus root, schisandra berry, lycium berry, cordyceps, American ginseng, suma root, licorice root, ginger rhizome, and tangerine peel;
    about 62.5 mg of acai berry;
    about 62.5 mg of maca root; and
    about 125 mg of a blend of ginger rhizome, turmeric rhizome, and cinnamon bark.

3. The composition of claim 1, wherein the powdered grass juices comprise juice derived from a green grass selected from the group consisting of wheat grass, Egyptian wheat grass, alfalfa grass, barley grass, oat grass, and combinations thereof.

4. The composition of claim 1, wherein the algae comprises green algae, blue-green algae, or a combination thereof.

5. The composition of claim 1, wherein the freeze-dried vegetable comprises spinach, broccoli, parsley, kale, tomato, or combinations thereof.

6. The composition of claim 1, wherein the source of vitamin C comprises a berry selected from the group consisting of acerola berry, camu camu berry, amla berry, acai berry, lycium berry, and combinations thereof.

7. The composition of claim 1, wherein the source of beta-glucans comprises a mushroom species selected from the group consisting of agaricus, cordyceps, maitake, reishi, shiitake, and combinations thereof.

8. The composition of claim 1, wherein the probiotic comprises lactic acid bacteria selected from the group consisting of *Lactobacillus acidophilus, Lactobacillus casei rhamnosus, Bifidobacterium longum, Streptococcus thermophilus, Lactobacillus plantarum*, and combinations thereof.

9. The composition of claim 1, wherein the prebiotic is selected from the group consisting of oat beta-glucan fiber, beet fiber, inulin, and combinations thereof.

10. The composition of claim 1, wherein the freeze-dried fruit is selected from the group consisting of strawberry, raspberry, blueberry, tart cherry, pomegranate, cranberry, and combinations thereof.

11. The composition of claim 1, wherein the source of polyphenols comprises green tea, white tea, or a combination thereof.

12. The composition of claim 1, wherein the source of oligomeric proanthocyanidins comprises a grape seed extract.

13. The composition of claim 1, wherein the source of silymarin comprises milk thistle.

14. The composition of claim 1, wherein the source of chlorogenic acids comprises artichokes.

15. The composition of claim 1, wherein the adaptogenic herb comprises an herb selected from the group consisting of Eleuthero root bark, Rhodiola root, Jiaogulan/Gynostemma aerial part, Reishi fruiting body, Holy Basil leaf, Ashwagandha root, Astragalus root, Schisandra berry, Cordyceps, American Ginseng, Suma root, Licorice root, Ginger rhizome, Tangerine peel, and combinations thereof.

16. The composition of claim 1, wherein the superfood comprises acai berry, maca root, or a combination thereof.

17. The composition of claim 1, wherein the medicinal rhizome comprises ginger, turmeric, or a combination thereof.

18. A method for supplementing the diet, comprising:
    administering to an individual an effective amount of the composition of claim 1 having an ORAC value of at least 4,500 per serving.

19. The method in accordance with claim 18, wherein a serving of the composition provides an equivalent of about twenty-four servings of fruits, vegetables, or a combination thereof or an ORAC value of at least 12,000.

* * * * *